(12) United States Patent
Britton et al.

(10) Patent No.: US 7,932,274 B2
(45) Date of Patent: Apr. 26, 2011

(54) 3-INDAZOLYL-4-PYRIDYLISOTHIAZOLES

(75) Inventors: Thomas Charles Britton, Carmel, IN (US); Veronique Dehlinger, Weybridge (GB); Adam Michael Fivush, Fishers, IN (US); Sean Patrick Hollinshead, Indianapolis, IN (US); Benjamin Paul Vokits, New York, NY (US)

(73) Assignee: Eli Lilly and Company, Indianapolis, IN (US)

( * ) Notice: Subject to any disclaimer, the term of this patent is extended or adjusted under 35 U.S.C. 154(b) by 296 days.

(21) Appl. No.: 12/406,139

(22) Filed: Mar. 18, 2009

(65) Prior Publication Data
US 2009/0253750 A1    Oct. 8, 2009

Related U.S. Application Data

(60) Provisional application No. 61/042,394, filed on Apr. 4, 2008.

(51) Int. Cl.
*A61K 31/4439* (2006.01)
*C07D 417/04* (2006.01)
(52) U.S. Cl. .................. 514/338; 546/271.1
(58) Field of Classification Search ............ 546/271.1; 514/338
See application file for complete search history.

(56) References Cited

U.S. PATENT DOCUMENTS

| 4,075,001 A | 2/1978 | Gibbons |
| 5,538,939 A | 7/1996 | Muenster et al. |
| 2006/0194807 A1 | 8/2006 | Cosford |

FOREIGN PATENT DOCUMENTS

| EP | 0129407 | 12/1984 |
| EP | 1247810 A | 10/2002 |
| WO | WO 00/24739 | 5/2000 |
| WO | 2007061909 A | 5/2007 |
| WO | WO 2008/103185 A2 | 8/2008 |
| WO | 2008128951 A | 10/2008 |

OTHER PUBLICATIONS

Slassi, Abdelmalik et al., Recent Advances in Non-Competitive mGlu5 Receptor Antagonists and their Potential Therapeutic Applications, *Current Topics in Medicinal Chemistry*, 2005, 5, pp. 897-911.

De Paults et al: Substituent effects of N-(1,3-diphenyl-1H-pyrazol-5-yl)benzamides on positive allosteric modulation on the metabotropic glutamate-5 receptor in rat cortical astrocytes, Journal of Medicinal Chemistry, American Chemical Society, vol. 49, Jan. 1, 2006, pp. 3332-3344.

*Primary Examiner* — Patricia L Morris
(74) *Attorney, Agent, or Firm* — Mark A. Winter

(57) ABSTRACT

The present invention provides 3-indazoyl-4-pyridylisothiazoles or a pharmaceutically acceptable salt thereof, pharmaceutical compositions thereof, and methods of using the same, as well as processes for preparing the same, and intermediates thereof.

12 Claims, No Drawings

3-INDAZOLYL-4-PYRIDYLISOTHIAZOLES

This application claims the benefit of U.S. Provisional Application No. 61/042,394, filed Apr. 4, 2008.

The present invention provides certain 3-indazoyl-4-pyridylisothiazoles, particularly certain N-acylated 5-amino-3-indazoyl-4-pyridylisothiazole derivatives, pharmaceutical compositions thereof, methods of using the same, processes for preparing the same, and intermediates thereof.

L-Glutamate is the major excitatory neurotransmitter in the central nervous system and is referred to as an excitatory amino acid. Glutamate receptors are composed of two major subtypes: the ligand-gated ion-channel ionotropic receptors, and the G-protein-coupled seven-transmembrane-domain metabotropic receptors (mGluRs). The metabotropic family comprises eight members and is sub-divided into three groups based on sequence similarity, signal transduction, and pharmacology. Group I receptors (mGluR$_1$; and mGluR$_5$, and their splice variants) are positively coupled to inositol phosphate hydrolysis and the generation of an intracellular calcium signal. Group II receptors (mGluR$_2$; and mGluR$_3$) and Group III receptors (mGluR$_4$, mGluR$_6$, mGluR$_7$, and mGluR$_8$) are negatively coupled to adenylyl cyclase and regulate cyclic AMP levels by indirectly inhibiting adenylyl cyclase activity. The mGlu receptor subtypes have unique expression patterns in the central nervous system, which can be targeted with new and selective agents. See, for example, Slassi, A. et. al., Current Topics in Medicinal Chemistry (2005), 5, 897-911, in which mGluR$_5$; antagonists are described as useful as (anti)anxiety agents in animal models related to stress. Also, mGluR$_5$; antagonists have been shown to be useful in models of substance dependence and withdrawal including alcohol self-administration, as well as models of inflammatory and neuropathic pain.

The compounds of the present invention are selective antagonists of the Group I metabotropic receptors, particularly the mGluR$_5$; receptor (mGluR$_5$), especially with respect to mGluR$_2$, mGluR$_3$; and mGluR$_4$; and they may be selective with respect to mGluR$_1$. As such they are believed to be useful for the treatment of conditions associated with those metabotropic glutamate receptors, such as anxiety including generalized anxiety disorder, depression including major depressive disorders, as well as anxiety co-morbid with depression (mixed anxiety depression disorder) including generalized anxiety disorder co-morbid with major depressive disorder.

Thus, the present invention provides new compounds that are antagonists of mGluR$_5$; and, as such, are believed to be useful in treatment of the disorders discussed above. Such new compounds could address the need for safe and effective treatments of conditions associated with the above receptors without attending side effects.

The present invention provides a compound of formula I, or a pharmaceutically acceptable salt thereof,

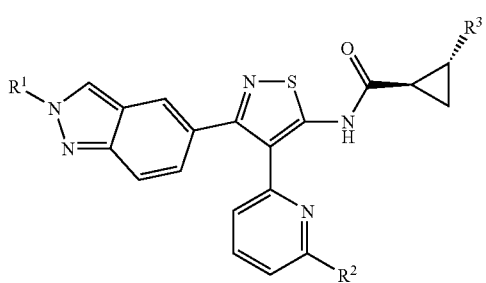

I wherein
R$^1$; is H or C$_1$-C$_3$; alkyl;
R$^2$; is H, C$_1$-C$_3$; alkyl, C$_3$-C$_5$; cycloalkyl, C$_1$-C$_3$; fluoroalkyl, NR$^4$R$^5$, C$_1$-C$_3$ alkoxy or C$_1$-C$_3$; alkoxymethyl;
R$^3$; is H or methyl; and
R$^4$; and R$^5$; are independently H or C$_1$-C$_3$; alkyl.

Further, the present invention provides a pharmaceutical composition comprising a compound of formula I, or a pharmaceutically acceptable salt thereof, and a pharmaceutically acceptable carrier, diluent or excipient.

Further, the present invention provides a compound of formula I, or a pharmaceutically acceptable salt thereof, for use in therapy.

Further, the present invention provides the use of a compound of formula I, or a pharmaceutically acceptable salt thereof, for the manufacture of a medicament for treating anxiety.

Further, the present invention provides a method of treating anxiety, comprising administering to a patient in need thereof an effective amount of a compound of formula I, or a pharmaceutically acceptable salt thereof.

Further, the present invention provides a compound of formula I, or a pharmaceutically acceptable salt thereof, for use in the treatment of anxiety.

The term "C$_1$-C$_3$; fluoroalkyl" refers to a straight or branched alkyl chain having from one to three carbon atoms substituted with one to three fluorine atoms and includes fluoromethyl, difluoromethyl and 1-fluoro-1-methyl-ethyl.

A particular compound of formula I is one wherein R$^1$; is C$_1$-C$_3$; alkyl. A particular compound of formula I is one wherein R$^2$; is C$_1$-C$_3$; alkyl.

A particular compound of formula I is one wherein R$^1$; is C$_1$-C$_3$; alkyl; R$^2$; is C$_1$-C$_3$; alkyl, C$_3$-C$_5$; cycloalkyl or C$_1$-C$_3$; fluoroalkyl; and R$^3$; is methyl.

A particular compound of formula I is one wherein R$^1$; is C$_1$-C$_3$; alkyl; R$^2$; is C$_1$-C$_3$; alkyl; and R$^3$; is methyl.

A particular compound of formula I is one wherein
R$^1$; is H, methyl or ethyl;
R$^2$; is H, methyl, ethyl, propyl, isopropyl, cyclopropyl, cyclobutyl, cyclopentyl, fluoromethyl, difluoromethyl, 1-fluoro-1-methyl-ethyl, methylamino, dimethylamino, methoxy or methoxymethyl; and R$^3$; is H or methyl.

A more particular compound of formula I is one wherein R$^1$; is methyl.

A more particular compound of formula I is one wherein R$^2$; is ethyl.

A more particular compound of formula I is one wherein R$^2$; is isopropyl.

A more particular compound of formula I is one wherein R$^3$; is methyl.

A preferred compound of formula I is (1R,2R)-2-methyl-cyclopropanecarboxylic acid [4-(6-ethyl-pyridin-2-yl)-3-(2-methyl-2H-indazol-5-yl)-isothiazol-5-yl]amide or pharmaceutically acceptable salt thereof.

A preferred compound of formula I is (1R,2R)-2-methyl-cyclopropanecarboxylic acid [4-(6-ethyl-pyridin-2-yl)-3-(2-methyl-2H-indazol-5-yl)-isothiazol-5-yl]amide hydrochloride.

A more preferred compound of formula I is (1R,2R)-2-methyl-cyclopropanecarboxylic acid [4-(6-isopropyl-pyridin-2-yl)-3-(2-methyl-2H-indazol-5-yl)-isothiazol-5-yl]-amide or a pharmaceutically acceptable salt thereof.

An even more preferred compound of formula I is (1R,2R)-2-methyl-cyclopropanecarboxylic acid [4-(6-isopropyl-pyridin-2-yl)-3-(2-methyl-2H-indazol-5-yl)-isothiazol-5-yl]-amide.

A further embodiment of the present invention include a process for preparing a compound of formula I, or a pharmaceutically acceptable salt thereof, comprising A) for a compound of formula I where $R^1$; is $C_1$-$C_3$; alkyl,

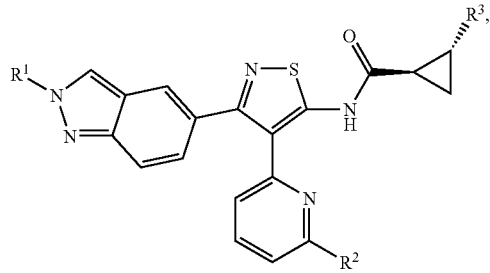

I $R^1$; is $C_1$-$C_3$; alkyl coupling of a compound of formula II where $R^1$; is $C_1$-$C_3$; alkyl with a 2-Q'-pyridyl where Q' is tri-n-butylstannanyl or trimethylstannanyl;

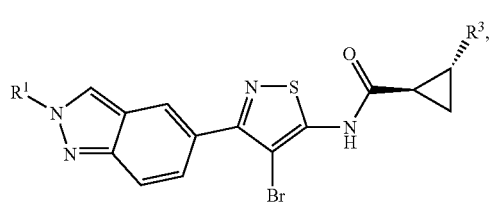

II $R^1$; is $C_1$-$C_3$; alkyl

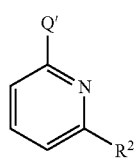

2-Q'-pyridyl where Q' is tri-n-butylstannanyl or trimethylstannanyl or

B) for a compound of formula I where $R^1$; is H,

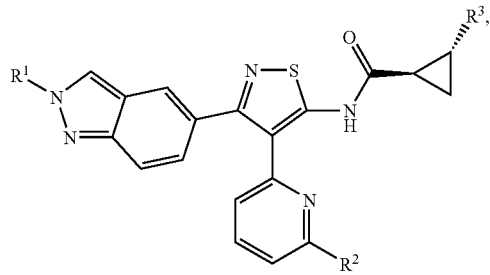

I $R^1$; is H deprotecting a compound of formula IV where P is t-butyloxycarbonyl;

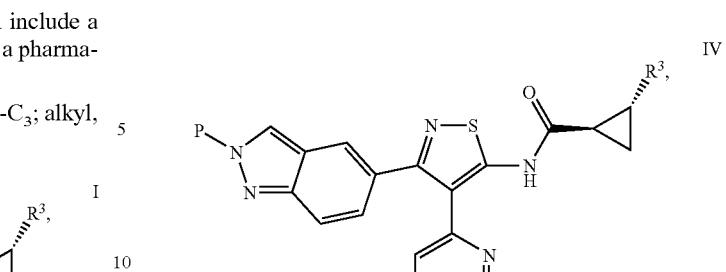

IV

P is t-butyloxycarbonyl whereafter, when a pharmaceutically acceptable salt of the compound of formula I is required, it is obtained by reacting a basic compound of formula I with a physiologically acceptable acid or by any other conventional procedure.

A further embodiment of the present invention provides intermediate compounds useful for the preparation of a compound of formula I. More specifically, the present invention provides a compound of formula II

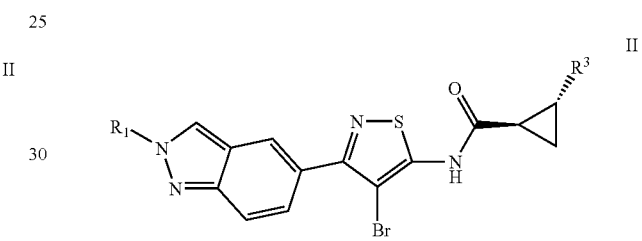

II wherein
$R^1$; is H or $C_1$-$C_3$; alkyl; and
$R^3$; is H or methyl.

A particular compound of formula II is one wherein $R^1$; is methyl.

A particular compound of formula II is one wherein $R^3$; is methyl.

A preferred compound of formula II is (1R,2R)-2-methyl-cyclopropanecarboxylic acid [4-bromo-3-(2-methyl-2H-indazol-5-yl)-isothiazol-5-yl]-amide.

It is understood that compounds of the present invention may exist as stereoisomers. While all enantiomers, diastereomers, and mixtures thereof, are contemplated within the present invention, preferred embodiments are single diastereomers, and more preferred embodiments are single enantiomers. It is understood for compounds of the present invention where $R^3$; is H, the cyclopropanecarboxylic acid amide group attached at the 5; position of the isothiazole is achiral.

A particular enantiomer of compounds of the present invention is one where the group attached at the 5; position of the isothiazole is a (1R,2R)-2-methyl-cyclopropane-carboxylic acid amide.

It is understood that compounds of the present invention may exist as tautomeric forms. When tautomeric forms exist, each form and mixtures thereof, are contemplated in the present invention. For example, when the group $R^1$; is hydrogen, a compound of formula I may exist in tautomeric forms I and II. As such, it is understood any reference to a compound of formula I where the group $R^1$; is hydrogen as tautomeric form I encompasses tautomeric form II as well as mixtures of forms I and II.

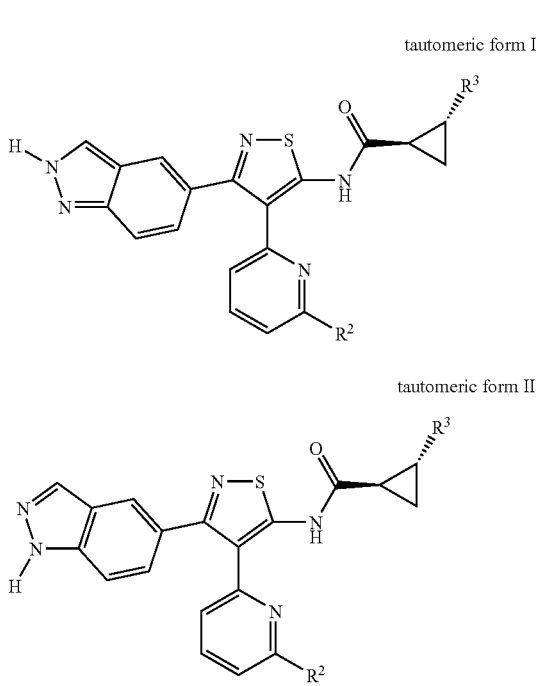

tautomeric form I tautomeric form II

The term "pharmaceutically acceptable salt" includes acid addition salt that exists in conjunction with the basic portion of a compound of formula I. Such salts include the pharmaceutically acceptable salts listed in HANDBOOK OF; PHARMACEUTICAL; SALTS: PROPERTIES, SELECTION AND; USE, P. H. Stahl and C. G. Wermuth (Eds.), Wiley-VCH, New York, 2002; which are known to the skilled artisan.

In addition to pharmaceutically acceptable salts, other salts are included in the invention. They may serve as intermediates in the purification of compounds or in the preparation of other pharmaceutically-acceptable salts, or are useful for identification, characterization or purification.

A compound of the invention is expected to be useful whenever antagonism of the mGluR$_5$; receptor is indicated. In particular, a compound of the invention is expected to be useful for the treatment of anxiety including generalized anxiety disorder, depression including major depressive disorder as well as anxiety co-morbid with depression (mixed anxiety depression). Accordingly, one particular aspect of the invention is treatment of mixed anxiety depression disorder including generalized anxiety disorder co-morbid with major depressive disorder.

As used herein, the term "patient" refers to a warm blooded animal such as a mammal and includes a human.

It is also recognized that one skilled in the art may affect an anxiety disorder by treating a patient presently displaying symptoms with an effective amount of the compound of formula I. Thus, the terms "treatment" and "treating" are intended to refer to all processes wherein there may be a slowing, interrupting, arresting, controlling, or stopping of the progression of the disorder and/or symptoms thereof, but does not necessarily indicate a total elimination of all symptoms.

It is also recognized that one skilled in the art may affect an anxiety disorder by treating a patient at risk of future symptoms with an effective amount of the compound of formula I and is intended to include prophylactic treatment of such.

As used herein, the term "effective amount" of a compound of formula I refers to an amount, that is, the dosage which is effective in treating an anxiety disorder described herein.

The attending diagnostician, as one skilled in the art, can readily determine an effective amount by the use of conventional techniques and by observing results obtained under analogous circumstances. In determining an effective amount, the dose of a compound of formula I, a number of factors are considered by the attending diagnostician, including, but not limited to the compound of formula I to be administered; the co-administration of other agents, if used; the species of mammal; its size, age, and general health; the degree of involvement or the severity of anxiety; the response of the individual patient; the mode of administration; the bioavailability characteristics of the preparation administered; the dose regimen selected; the use of other concomitant medication; and other relevant circumstances.

An effective amount of a compound of formula I is expected to vary from about 0.01; milligram per kilogram of body weight per day (mg/kg/day) to about 5; mg/kg/day. Preferred amounts may be determined by one skilled in the art.

The compounds of the present invention can be administered alone or in the form of a pharmaceutical composition, that is, combined with pharmaceutically acceptable carriers or excipients, the proportion and nature of which are determined by the solubility and chemical properties, including stability, of the compound selected, the chosen route of administration, and standard pharmaceutical practice. The compounds of the present invention, while effective themselves, may be formulated and administered in the form of their pharmaceutically acceptable salts, for convenience of crystallization, increased solubility, and the like.

Thus, the present invention provides pharmaceutical compositions comprising a compound of the formula I and a pharmaceutically acceptable carrier, diluent or excipient.

One skilled in the art of preparing formulations can readily select the proper form and mode of administration depending upon the particular characteristics of the compound selected, the disorder or condition to be treated, the stage of the disorder or condition, and other relevant circumstances (REMINGTON:; THE; SCIENCE AND; PRACTICE OF PHARMACY, 19th Edition, Mack Publishing Co. (1995)).

EXAMPLE A

Functional in Vitro Activity at Human mGluR$_5$; and mGluR$_1$; Receptors

The activation of G-protein coupled receptors (GPCRS) that are coupled to GTP-binding protein alpha q (Gq proteins) results in a change in intracellular calcium concentration. This functional response can be measured in a kinetic assay using calcium-sensitive dyes and a fluorescent imaging plate reader using a standard technique known as FLIPR (MDS Analytical Technologies, Sunnyvale, Calif.). Stable cell line preparation and assay techniques are adapted from Kingston, A. E., et. al. (1995) Neuropharmacology 34: 887-894.

Briefly, clonal cell lines expressing recombinant human mGluR$_{5a}$; and mGluR$_{1\alpha}$; receptors are transfected into AV-12; cells (American Type Culture Collection, Manassas, Va.) containing the rat EAAT 1; glutamate transporter. Cells are grown in Dulbecco's Modified Eagle's Medium supplemented with 5% fetal bovine serum, 1; mM L-glutamine, 1; mM sodium pyruvate, 10; mM HEPES (4-(2-hydroxyethyl)-1-piperazineethanesulfonic acid), 0.75; mg/ml geneticin, and 0.3; mg/ml hygromycin B at 37° C. in an incubator with 95% relative humidity and 5% $CO_2$. Confluent cultures are passaged biweekly.

For the functional assays, cells are seeded in growth medium lacking selection antibiotics at a density of 65K per well into 96-well, black/clear bottom, poly-D-lysine coated microplates and incubated for 18-20; hours prior to the experiment. After removing the medium, cells are dye-loaded with 8; µM Fluo-3; in assay buffer consisting of Hanks Balanced Salt Solution supplemented with 20; mM HEPES for 1.5; hr at 25° C. Compounds are serially diluted into DMSO and then diluted once into assay buffer; the final DMSO concentration in the assay is 0.625%. A single-addition FLIPR assay generating an 11-point dose response curve for the agonist glutamate is conducted prior to each experiment to estimate the amount of agonist needed to induce an $EC_{90}$; response. The antagonist effects of compounds are quantified in the FLIPR instrument in 10-point dose curves by comparing the peak fluorescent responses to the agonist glutamate in the presence and absence of compound. Specifically, the compound effect is measured as maximal minus minimal peak heights in relative fluorescent units corrected for basal fluorescence as measured in the absence of glutamate. Activity data at the human $mGluR_5$; and $mGluR_1$; receptors are calculated as relative $IC_{50}$; values using a four-parameter logistic curve fitting program (ActivityBase® v5.3.1.22).

In the above assay, compounds exemplified herein exhibit an $IC_{50}$; of less than 75; nM at $mGluR_5$. For example, the compound of Example 2; has an $IC_{50}$; of 9.5; nM measured at $mGluR_5$. This demonstrates that compounds of the present invention are potent $mGluR_5$; antagonists.

EXAMPLE B

Attenuation of Stress-Induced Hyperthermia in Rats

Hyperthermia, a rise in core body temperature, is a general phenomenon that has been reliably demonstrated in many mammals, including humans, in response to stress. In many anxiety disorders, hyperthermia occurs as part of the pathology and is considered a symptom of the disease. Compounds which attenuate stress-induced hyperthermia in animals are believed to be useful in treating anxiety disorders in humans.

The conventional and minimally-invasive method for analyzing stress-induced hyperthermia is by measuring body temperature, and stress-induced increases in body temperature, via rectal thermometer. Male Fischer F-344; rats (Harlan, Indianapolis, Ind., USA) weighing between 275-350; g are tested. All animals are individually-housed with food and automated water available ad libitum, and maintained on a 12; h light/dark cycle (lights on at 06:00). Animals are fasted for approximately 12-18; hours before the experiment, which is conducted during the light phase. Rats are dosed p.o. in a dose volume of 1; mL/kg with test compounds in the range of 0.3, 1, 3, and 10; mg/kg (suspended in 1% carboxymethylcellulose, 0.25% polysorbate 80, 0.05% antifoam). The $mGluR_5$; antagonist MTEP (3-[(2-methyl-1,3-thiazol-4-yl)ethynyl] pyridine), which has demonstrated robust anxiolytic-like activity in preclinical models, is used as a positive control (10; mg/kg, p.o., dissolved in water). Immediately following dosing, rats are returned to their home cage, and the experimenter turns off the lights and leaves the room. The dosing room is darkened for the remainder of the 60; min pretreatment period.

After the pretreatment period, rats are taken individually to a brightly lit adjacent room where baseline body temperatures are determined by insertion of a rectal probe lubricated with mineral oil. Body temperature is assessed using a PHYSITEMP BAT-12® Microprobe Thermometer with a PHYSITEMP RET-2® rat rectal probe (Physitemp Instruments Inc., Clifton, N.J., USA). The probe is inserted approximately 2; cm into the rectum, to measure the core body temperature (this is the baseline body temperature, T1, in degrees Celsius). Ten minutes later a second body temperature measurement is recorded (T2). The difference in body temperature (T2−T1) is defined as the stress-induced hyperthermic response. The dose at which a compound produces a 35% reduction in stress-induced hyperthermic response, relative to the vehicle response, is defined as the T35; dose. In the above assay, the compound of Example 2; produces a reduction in stress-induced hyperthermia with a T35; dose=3.0; mg/kg. This demonstrates that compounds of the present invention are useful in an in vivo model of anxiety.

A compound of formula I may be prepared by processes which include processes known in the chemical art for the production of structurally analogous compounds or by a novel process described herein. A novel process described herein provides another aspect of the invention. A process for the preparation of a compound of formula I, or a pharmaceutically acceptable salt thereof, and novel intermediates for the manufacture of a compound of formula I provide further features of the invention and are illustrated by the following procedures in which the meaning of the generic radicals are as defined above, unless otherwise specified.

Generally, a compound of formula I may be prepared from a compound of formula III (Scheme 1). More specifically, a compound of formula II where $R^1$; is $C_1$-$C_3$ alkyl is coupled with a 2-Q'-pyridyl where Q' represents a suitable coupling group in the presence of a coupling catalyst to provide a compound of formula I where $R^1$; is $C_1$-$C_3$ alkyl. The suitability of the coupling group Q' is guided by the reaction conditions employed. For reactions employing Suzuki conditions, the values of Q' include boronic ester and acid derivatives whereas employing Stille conditions, the values of Q' include trialkylstannanyl derivatives. Further coupling reactions include those employing Negishi conditions where the values of Q' include zinc halides such as zinc bromide. Coupling catalysts include transition metal agents such as palladium derivatives.

A compound of formula II may be prepared from a compound of formula III. More specifically, a compound of formula III is coupled with a 5-Q"-indazolyl where $R^1$ is $C_1$-$C_3$; alkyl and Q" represents a suitable coupling group in the presence of a coupling catalyst to provide a compound of formula II where $R^1$; is $C_1$-$C_3$; alkyl. The suitability of the coupling group Q" is guided by the reaction conditions employed. For reactions employing Suzuki conditions, the values of Q" include boronic ester and acid derivatives; whereas employing Stille conditions, the values of Q" include trialkylstannanyl derivatives. Coupling catalysts include transition metal agents such as palladium derivatives.

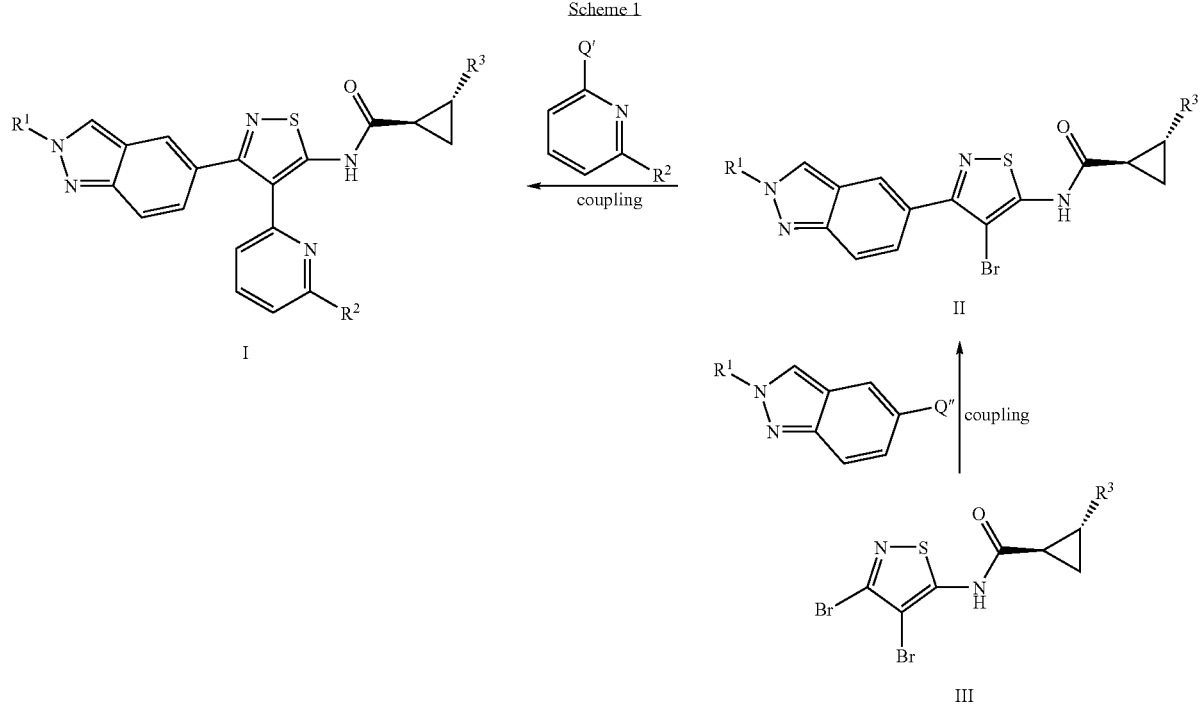

Generally, a compound of formula I where $R^1$; is H may be prepared from a compound of formula III (Scheme 2). More specifically, a compound of formula IV where P is a suitable amino protecting group such as t-butyloxycarbonyl is reacted with an acid such as hydrochloric acid to provide a compound of formula I where $R^1$; is H. A compound of formula IV where P is an amino protecting group may be prepared from a compound of formula V. More specifically, a compound of formula V is coupled with a 2-Q'-pyridyl where Q' represents a suitable coupling group in the presence of a coupling catalyst to provide a compound of formula IV where P is an amino protecting group. The suitability of the coupling group Q' is guided by the reaction conditions employed. For reactions employing Suzuki conditions, the values of Q' include boronic ester and acid derivatives; whereas employing Stille conditions, the values of Q' include trialkylstannanyl derivatives. Coupling catalysts include transition metal agents such as palladium derivatives. A compound of formula V may be prepared by coupling a compound of formula III with a 5-Q"-indazolyl where P is an amino protecting group and Q" represents a suitable coupling group in the presence of a coupling catalyst to provide a compound of formula V where P is an amino protecting group. The suitability of the coupling group Q" is guided by the reaction conditions employed. For reactions employing Suzuki conditions, the values of Q" include boronic ester and acid derivatives; whereas employing Stille conditions, the values of Q" include trialkylstannanyl derivatives. Coupling catalysts include transition metal agents such as palladium derivatives.

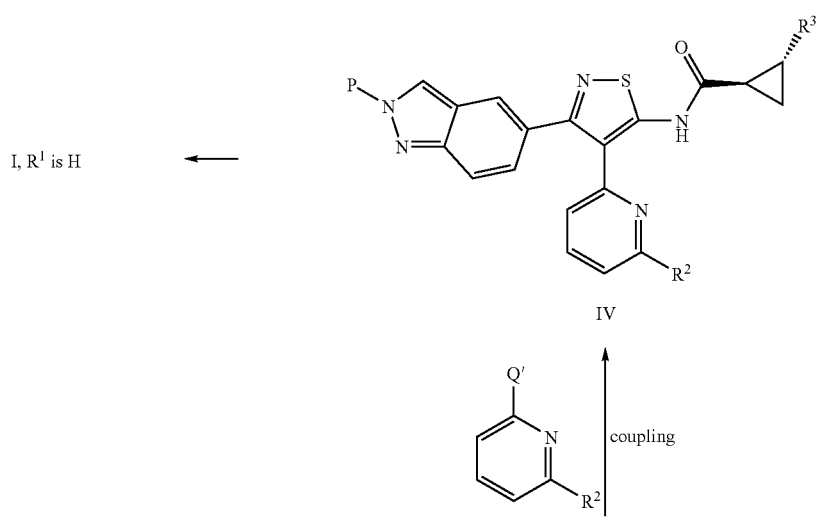

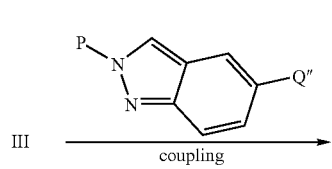 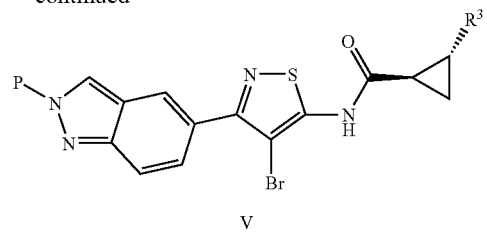

In the following illustrative preparations and examples, the following meanings and abbreviations are used throughout: DMSO, dimethyl sulfoxide (perdeuterated [-d₆] if for NMR); MS, mass spectrum; EtOAc, ethyl acetate; THF, tetrahydrofuran; min, minutes; HPLC, high pressure liquid chromatography; LC-MS, HPLC-mass spectrography; GC, gas chromatography; MeOH, methanol; MTBE, methyl t-butyl ether; SCX-2, cation exchange resin; mp, melting point; and NMR, nuclear magnetic resonance spectroscopy or spectrum. Reagents were obtained from a variety of commercial sources. Solvents are generally removed under reduced pressure (evaporated). In some preparations indicated yields are representative crude yields for products which are isolated by evaporation or filtration and used directly without further purification.

Preparation 1

Synthesis of 5-bromo-2-methyl-2H-indazole

Add at room temperature under nitrogen, trimethyloxonium tetrafluoroborate (229.34; g, 1.52; mol) portion wise to a mixture of 5-bromo-1H-indazole (199.6; g, 1.01 mol) in ethyl acetate (3.04; L, 31.06; mol), stir 2.5; h and filter to give a white solid. Wash the recovered solid twice with ethyl acetate (500; mL) and then add it portion wise to a cooled aqueous solution of 2; M sodium hydroxide (3.80; L, 7.60; mol) in an ice bath. Stir the mixture for 1; h, sonicate for 15; min., filter and wash the recovered solid twice with water (200; mL). Dry the solid overnight under vacuum, slurry in dichloromethane (1; L) and filter. Concentrate the filtrate and purify by silica gel chromatography eluting with dichloromethane to give the title compound as a yellow solid (149.77; g, 70%). MS (m/z): 211, 213; (M+1).

The following compound is prepared essentially as described in Preparation 1.

| Preparation | Name | Data |
|---|---|---|
| 2 | 5-bromo-2-ethyl-2H-indazole | MS (m/z): 225, 227 (M + 1) |

Preparation 3

Synthesis of 2-methyl-5-(4,4,5,5-tetramethyl-[1,3,2]dioxaborolan-2-yl)-2H-indazole Add potassium acetate (207.16; g, 2.11; mol) in one portion to a stirring solution of 5-bromo-2-methyl-2H-indazole (148.5; g, 0.703; mol) and bis(pinacolato)diboron (196.54 g, 0.77; mol) in 1,4-dioxane (1.62; L). Bubble nitrogen through the suspension for 20; min, add (1,1'-bis(diphenylphosphino) ferrocene)palladium(II) chloride:dichloromethane (17.24; g, 21.11; mmol) in one portion and heat at 100° C. for 1.5; h. Cool, filter through Celite® using ethyl acetate (1; L) and concentrate. Purify the residue by silica gel chromatography, gradient eluting from 50:50; to 20:80; using n-hexane:methyl t-butyl ether to give the title compound as a yellow solid (124.79; g, 64%) which is used without further purification. Concentrate impure fractions and triturate the recovered solid with n-heptane to give additional amounts of the title compound as a white solid (32.36; g, 12%). ¹H-NMR (DMSO-d₆): δ1.30; (s, 12H), 4.17; (s, 3H), 7.43; (dd, 1H), 7.53 (dd, 1H), 8.14; (t, 1H), 8.39; (s, 1H).

Preparation 4

Synthesis of 2-methyl-5-trimethylstannanyl-2H-indazole

Add tetrakis(triphenylphosphine)palladium (0.26; g, 0.22; mmol) to a mixture of 5-bromo-2-methyl-2H-indazole (0.94; g, 4.43; mmol) and hexamethylditin (1.02; mL, 4.88 mmol) in 1,4-dioxane (5; mL). Flush with nitrogen and heat in a microwave at 110° C. for 15; min. Prepare similarly two other batches from respectively tetrakis(triphenyl-phosphine)palladium (0.29; g, 0.25; mmol), 5-bromo-2-methyl-2H-indazole (1.07; g, 5.07 mmol), hexamethylditin (1.16; mL, 5.58; mmol) in 1,4-dioxane (5; mL) and tetrakis(triphenylphosphine)palladium (0.25; g, 0.22; mmol), 5-bromo-2-methyl-2H-indazole (0.92; g, 4.36; mmol), hexamethylditin (1.00; mL, 4.80; mmol) in 1,4-dioxane (5 mL). Combine the three batches and purify by silica gel chromatography gradient eluting from 15:85; to 80:20; using ethyl acetate:iso-hexane, and then further purify with a second silica gel chromatography, gradient eluting from 15:85; to 30:70; using ethyl acetate:iso-hexane to give the title compound as an oil which crystallizes on standing (1.68; g, 41%). MS (m/z): 293-301; cluster (M+1).

The following compound is prepared essentially as described in Preparation 4.

| Preparation | Name | Data |
|---|---|---|
| 5 | 2-ethyl-5-trimethylstannanyl-2H-indazole | MS (m/z): 307-315 cluster (M + 1). |

Preparation 6

Synthesis of 5-bromo-indazole-1-carboxylic acid tert-butyl ester

Sequentially add triethylamine (7.1; mL, 50.75; mmol), di-tert-butyl dicarbonate (17.12; g, 76.13; mmol) and dimethyaminopyridine (0.62; g, 5.08; mmol) to a solution of 5-bromo-1H-indazole (10; g, 50.75; mmol) in acetonitrile (170; mL) and stir 3; hours. Concentrate and purify by silica gel chromatography, gradient eluting from 10:90; to 20:80; using ethyl acetate:hexanes, to give the title compound (14.93; g, 99%). MS (m/z): 243; (M+1-tBu).

Preparation 7

Synthesis of 5-trimethylstannanyl-indazole-1-carboxylic acid tert-butyl ester

Dissolve 5-bromo-indazole-1-carboxylic acid tert-butyl ester (6.5; g, 21.87; mmol) in toluene (43.7; mL) and add hexamethylditin (10; g, 30.6; mmol) under a blanket of nitrogen. Add tetrakis(triphenylphosphine)palladium (1.26; g, 1.09; mmol), heat at 80° C. for 18; hours, concentrate and purify the residue by silica gel chromatography, gradient eluting from 10:90; to 20:80; using ethyl acetate:hexanes, to give the title compound (9.33 g, 94%). MS (m/z): 327; (M+1-tBu).

Preparation 8

Synthesis of 2-cyano-3-oxo-thiobutyramide

To a stirring solution of 2-cyano-thioacetamide, (1016; g, 9.84; mol) in pyridine (2.60; L), chilled to 0° C., add acetyl chloride over 2; hours (785; mL, 11.03; mol) keeping reaction temperature below 20° C. Warm to room temperature over 1; hour, add water (4; L) and stir until dissolution of all solids. Add an aqueous 12; M solution of hydrochloric acid (HCl, 250; mL) until acidic (pH=1) to give a red-brown precipitate. Stir for 1; hour at 0° C., filter, dry the collected solid under vacuum to give the title compound as an orange solid (926; g, 66%). A second crop can be harvested from the mother liquors by adding 12; M aqueous (500; mL) to give the title compound (353; g, 25%).

Preparation 9

Synthesis of 1-(5-amino-3-bromo-isothiazol-4-yl)-ethanone

Add bromine (195; mL, 3.81; mol) over 10; min to a heated solution of 2-cyano-3-oxo-thiobutyramide (550; g, 3.86; mol) in glacial acetic acid (5.80; L) at 40° C. and stir at room temperature for 15; h. Filter the reaction mixture, wash the collected solid with water and dry overnight under vacuum to give a dark red solid (1151; g). Slurry the solid with stirring in a saturated aqueous solution of sodium bicarbonate (8; L) for 30; min and filter. Wash the collected solid with water and dry overnight under vacuum to give a dark red solid (1022; g). Slurry the solid with stirring with methyl t-butyl ether (5.90; L) over 1 hour, filter and retain the filtrate. Repeat the above methyl t-butyl ether extraction process twice on recovered solid retaining the filtrate after each extraction. Combine the filtrates and concentrate to give the title compound as a yellow solid which is carried on without further purification (598; g, 72%). MS (m/z): 221, 223; (M+1).

Preparation 10

Synthesis of (1R,2R)-2-methyl-cyclopropanecarboxylic acid

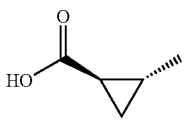

Add methyl tert-butyl ether (13.2; L) to a suspension of (1R,2R)-2-methyl-cyclopropanecarboxylic acid, dicyclohexylammonium salt (1.65; kg, 5.86; mol), prepared as described in Organic Process Research & Development (2007) 11, 689-692, in water (6.60; L) and stir vigorously for 5; min to give a biphasic solution. Add sulfuric acid (200 mL) dropwise over 10; min, stir vigorously for 15; min and separate the layers. Extract the aqueous phase with methyl tert-butyl ether. Combine the organic phases, dry over magnesium sulfate, filter and concentrate to give the title compound as a pale yellow oil (560; g, 95%) which is used with out further purification. $^1$H NMR (CDCl$_3$) δ 0.77-0.73 (m, 1H), 1.12; (d, 3H), 1.25-1.21; (m, 1H), 1.34-1.30; (m, 1H), 1.49-1.43; (m, 1H).

Preparation 11

Synthesis of (1R,2R)-2-methyl-cyclopropanecarbonyl chloride

Add oxalyl chloride (490.23; mL, 5.54; mol) dropwise over 20; min to a cooled solution of (1R,2R)-2-methyl-cyclopropanecarboxylic acid (560; g, 5.59; mol) in dichloromethane (2.80; L) and dimethylformamide (2.16; mL, 28.0; mmol) at 0° C. Warm to room temperature over 30; min, heat at 40° C. for 30; min and cool to room temperature to give a pale orange solution which is used directly in the next synthetic step.

Preparation 12

Synthesis of (1R,2R)-2-methyl-cyclopropanecarboxylic acid (4-acetyl-3-bromoisothiazol-5-yl)-amide Add a freshly prepared 1.93M solution of (1R,2R)-2-methyl-cyclopropanecarbonyl chloride (5.52; mol) in dichloromethane over 15; min to a suspension of 1-(5-amino-3-bromo-isothiazol-4-yl)-ethanone (1.17; kg, 4.93; mol) and triethylamine (859; mL, 6.16; mol) in dichloromethane (5.86; L) at room temperature and stir 4; hours. Quench the reaction with water (1; L) and separate the layers. Dry the organic layer over magnesium sulfate, filter, concentrate and purify the residue by short column silica gel chromatography (3500; g of SiO$_2$) gradient eluting from 100:0; to 40:60 using n-hexane and ethyl acetate to give the title compound as a white solid (1230; g, 82%). MS (m/z): 303, 305; (M+1).

Preparation 13

Synthesis of cyclopropanecarboxylic acid (4-acetyl-3-bromo-isothiazol-5-yl)-amide Add triethylamine (234.5; mL, 1.68; mol) to a cooled suspension of 1-(5-amino-3-bromo-isothiazol-4-yl)-ethanone (310; g, 1.40; mol) in dichloromethane (2.79; L, 43.53 mol) at 0° C. under nitrogen and then add slowly a solution of cyclopropanecarbonyl chloride (137.5; mL, 1.47; mol) in dichloromethane (310; mL, 4.84; mol) at 0° C. over 1 hour. Warm to 16° C. over 2; hours and then cool to 10° C., add water (1; L) and separate the layers. Extract the aqueous layer once with dichloromethane (500; mL). Combine the organic layers, concentrate and purify by silica gel chromatography eluting with n-hexane:dichloromethane 30:70. Triturate the recovered solid with hexanes to give the title compound as a white solid (256.1; g, 60%). MS (m/z): 289, 291; (M+1).

Preparation 14

Synthesis of (1R,2R)-2-methyl-cyclopropanecarboxylic acid (3,4-dibromo-isothiazol-5-yl)-amide Add bromine (114; mL, 2.2; mol) dropwise over 45; min to a cooled aqueous solution of sodium hydroxide (4.6M, 3.84; L, 17.8; mol) at −10° C. and stir for 0.5; hour to give a yellow solution. Add this solution dropwise to a pre-cooled −5° C. solution of (1R,2R)-2-methyl-cyclopropanecarboxylic acid (4-acetyl-3-bromo-isothiazol-5-yl)-amide (150; g, 495; mmol) in 1,4-dioxane (2; L) and stir 45; min at 5-10° C. Maintain cooling at 10° C. whilst adding a 40% (wt/wt) aqueous solution of sodium bisulfite (47.5; mL) over 5 min, stir 5; min and add slowly 12; M hydrochloric acid (approximately 500; mL) over 15 min until acidic (pH=2). Dilute with ethyl acetate (2; L) and separate the layers. Extract the aqueous layer twice with ethyl acetate (1; L). Combine the organic phases, dry over magnesium sulfate, filter and concentrate. Dissolve the residue in dichloromethane (600 mL), dilute with n-hexane (3; L), and cool to 5° C. overnight. Filter and wash the recovered solid with four portions of n-hexane (125; mL) to give the title compound as a white solid (92.6; g, 55%). If desired a second crop of the title compound (50.97; g, 30%) can be harvested from the mother liquors. MS (m/z): 339, 341, 343; (M+1).

Preparation 15

Synthesis of cyclopropanecarboxylic acid (3,4-dibromo-isothiazol-5-yl)-amide

Add bromine (118.3; mL, 2.30; mol) over 1; hour to a cooled aqueous solution of sodium hydroxide (3.77; M, 2.44; L, 9.21; mol) at 0° C. and stir 15; min. To this solution, add a solution of cyclopropanecarboxylic acid (4-acetyl-3-bromo-isothiazol-5-yl)-amide (155.7; g, 0.51; mol) in 1,4-dioxane (856.3; mL, 10.03; mol) over 100; min maintaining the temperature below 5° C. Stir for 1.5; hour maintaining the internal temperature below 10° C. Add an aqueous solution of sodium bisulfite (77.8; mL, 0.377; mol), stir for 5; min and add 12; M hydrochloric acid (390.1; mL, 4.60; mol) over 15; minutes maintaining the temperature below 25° C. Hold the mixture without stirring for 10; min then remove the supernatant, filter the remaining suspension, wash the recovered solid twice with water (200; mL) and dry under vacuum to give the title compound as a yellow solid (91.21; g, 55%). MS (m/z): 325, 327, 329; (M+1).

Preparation 16

Synthesis of (1R,2R)-2-methyl-cyclopropane carboxylic acid [4-bromo-3-(2-methyl-2H-indazol-5-yl)-isothiazol-5-yl]-amide Add a 2; M aqueous solution of sodium carbonate (606.3; mL, 1.21; mol) to a stirring mixture of (1R,2R)-2-methyl-cyclopropanecarboxylic acid (3,4-dibromo-isothiazol-5-yl)-amide (148.1; g, 0.404; mol) and 2-methyl-5-(4,4,5,5-tetramethyl-[1,3,2]dioxaborolan-2-yl)-2H-indazole (123.40; g, 0.444; mol) in HPLC grade 1,2-dimethoxyethane (1.21; L) and degas using vacuum and nitrogen. Add bis(triphenylphosphine) palladium(II) dichloride (56.77; g, 80.84; mmol) in one portion, heat at 83° C. for 10; h, cool to room temperature and filter through a pad of Celite® using ethyl acetate to give a biphasic solution. Separate the layers and extract the aqueous layer three times with dichloromethane (200; mL). Combine all the organic layers, wash with brine (200; mL) and concentrate to approximately a volume of 400; mL. Separate into two portions and purify each by silica gel chromatography by gradient 50:50; to 10:90; eluting with n-hexane:ethyl acetate to give the title compound as a light brown solid (107.32; g, 51%). MS (m/z): 391,393; (M+1).

Alternative method for the synthesis of (1R,2R)-2-methyl-cyclopropanecarboxylic acid [4-bromo-3-(2-methyl-2H-indazol-5-yl)-isothiazol-5-yl]-amide.

Charge a round bottom flask with (1R,2R)-2-methyl-cyclopropanecarboxylic acid (3,4-dibromo-isothiazol-5-yl)-amide (2.55; g, 7.49; mmol), 2-methyl-5-trimethylstannanyl-2H-indazole (2.21; g, 7.49; mmol) and lithium chloride (0.95; g, 22.48; mmol) in 1,4-dioxane (19.2; mL). Purge with nitrogen for 20; min, add tetrakis(triphenylphosphine) palladium (1.31; g, 1.12; mmol) and heat at 105° C. for 48; h. Directly load reaction mixture onto a silica gel column and purify by gradient eluting from 0:100; to 100:0; ethyl acetate:iso-hexane to give the title compound (1.25; g, 43%). MS (m/z): 391, 393; (M+1).

The following compound is prepared essentially as described in alternative method of Preparation 16; using 2-ethyl-5-trimethylstannanyl-2H-indazole.

| Preparation | Name | Data |
|---|---|---|
| 17 | (1R,2R)-2-methyl-cyclopropanecarboxylic acid [4-bromo-3-(2-ethyl-2H-indazol-5-yl)-isothiazol-5-yl]-amide | MS (m/z): 405, 407 (M + 1) |

Preparation 18

Synthesis of 5-{4-bromo-5-[((1R,2R)-2-methyl-cyclopropanecarbonyl)-amino]-isothiazol-3-yl}-indazole-1-carboxylic acid tert-butyl ester Dissolve (1R,2R)-2-methyl-cyclopropanecarboxylic acid (3,4-dibromo-isothiazol-5-yl)-amide (3.0; g, 8.82; mmol) in anhydrous 1,4-dioxane (88; mL) and add 5-trimethylstannanyl-indazole-1-carboxylic acid tert-butyl ester (4. 11; g, 9.70; mmol). Blanket under nitrogen, add bis(triphenylphosphine) palladium(II) chloride (0.62; g, 0.88 mmol) and heat to 85° C. for 4; days. Concentrate and purify the residue by silica gel chromatography, gradient eluting from 20:80; to 40:60; ethyl acetate:hexanes to give the title compound (1.04; g, 70% purity wt/wt, 17%) which is carried on with out further purification. MS (m/z): 477, 479; (M+1).

Preparation 19

Synthesis of cyclopropanecarboxylic acid [4-bromo-3-(2-methyl-2H-indazol-5-yl)-isothiazol-5-yl]-amide Degas by bubbling nitrogen for 10; min through a mixture of cyclopropanecarboxylic acid (3,4-dibromo-isothiazol-5-yl)-amide (1.04; g, 3.19; mmol) and 2-methyl-5-(4,4,5,5-tetramethyl-[1,3,2]dioxaborolan-2-yl)-2H-indazole (1.29; g, 3.51 mmol) in 1,4-dioxane (16; mL) and a 2M aqueous solution of sodium carbonate (7.98 mL). Add bis(triphenylphosphine)palladium(II) chloride (448; mg, 0.64; mmol) and heat at 80° C. for 12; h. Cool, dilute with brine and ethyl acetate and separate the layers. Extract the aqueous phase twice with ethyl acetate. Dry the combined organic phases over sodium sulfate, filter, concentrate and purify by silica gel chromatography, gradient eluting from 40:60; to 100:0; using ethyl acetate:hexanes, to give the title compound as a solid (0.6; g, 1.59; mmol, 50%). MS (m/z): 377, 379; (M+1).

Preparation 20

Synthesis of 2-bromo-6-cyclopentyl-pyridine

Bubble nitrogen through a solution of copper (I) iodide (1.48; g, 7.77; mmol), 2,6-dibromopyridine (8; g, 33.77; mmol) and (1,1'-bis(diphenylphosphino)ferrocene) palladium(II) chloride (2.90; g, 3.55; mmol) in anhydrous tetrahydrofuran (40; mL) for 5; min. Add a 0.5; M solution of cyclopentyl zinc bromide in tetrahydrofuran (79.70; mL, 39.85; mmol) in one portion and stir overnight. Dilute with hexanes (800; mL) and filter through a plug of silica gel using a solution of ethyl acetate:hexanes (10:90), to give a clear solution. Concentrate, purify by reverse phase chromatography using a gradient of water (w/1% trifluoroacetic acid):acetonitrile, and combine fractions containing pure product. Add a saturated aqueous solution of sodium bicarbonate to the combined fractions until basic and extract with six portions of hexanes (150; mL). Dry the hexane layers over sodium sulfate, filter and concentrate to give the title compound as a clear liquid (3.75; g, 49%). MS (m/z): 226, 228; (M+1).

The following compounds are prepared essentially as described in Preparation 20 using cyclobutyl zinc bromide or cyclopropyl zinc bromide, respectively.

| Preparation | Name | Data |
|---|---|---|
| 21 | 2-bromo-6-cyclobutyl-pyridine | MS (m/z): 212, 214 (M + 1) |
| 22 | 2-bromo-6-cyclopropyl-pyridine | $^1$H NMR (CDCl$_3$) δ 1.01 (m, 4H), 1.98 (m, 1H), 7.04 (d, 1H), 7.19 (d, 1H), 7.35 (t, 1H). |

Preparation 23

Synthesis of 2-bromo-6-ethyl-pyridine

Add under nitrogen a solution of 2.5; M n-butyllithium in hexanes (186.74; mL, 0.467; mol) over 41; min to a solution of diisopropylamine (68.7; mL, 0.488; mol) in tetrahydrofuran (745; mL, 9.16; mol) at −78° C. (dry-ice/acetone bath). Stir for 15; min and add 2-bromo-6-methylpyridine (49.3; mL, 0.424; mol) dropwise over 22; min. Stir 15; min, add methyl iodide (52.87; mL, 0.848; mol) dropwise over 1; hour and then warm to room temperature over 1.5; hour. Add water (250; mL) while cooling with a dry-ice/acetone bath and separate the layers. Extract the aqueous phase twice with ethyl acetate (300 mL). Combine the organic phases, concentrate and purify by silica gel chromatography, gradient eluting from 100:0; to 80:20; using hexanes:ethyl acetate, to give the title compound as a yellow oil (59.74; g, 75%). $^1$H NMR (CDCl$_3$) δ 1.28; (t, 3H), 2.80; (q, 2H), 7.11; (d, 1H), 7.27; (d, 1H), 7.45; (t, 1H).

The following compounds are prepared essentially as described in Preparation 23.

| Preparation | Name | Data |
|---|---|---|
| 24 | 2-bromo-6-isopropyl-pyridine | MS (m/z): 200, 202 (M + 1). |
| 25 | 2-bromo-6-propyl-pyridine | $^1$H NMR (CDCl$_3$) δ 0.96 (t, 3H), 1.74 (m, 2H), 2.73 (t, 2H), 7.09 (d, 1H), 7.29 (d, 1H), 7.44 (t, 1H). |

Preparation 26

Synthesis of 2-bromo-6-methoxymethyl-pyridine

Add dropwise a solution of (6-bromo-pyridin-2-yl)-methanol (9.6; g, 51; mmol) in anhydrous tetrahydrofuran (29; mL) to a stirring suspension of sodium hydride (60% dispersion in oil, 2.45; g, 61; mmol) in anhydrous tetrahydrofuran (96; mL) cooled to 0-5° C. under nitrogen. After gas evolution ceases, add dropwise methyl iodide (10.9; mL, 77; mmol) and warm to room temperature over 1; hour. Add iced water (100; mL), dilute with brine (100; mL) and ethyl acetate (200; mL). Separate the layers. Extract the organic layer once with brine (100; mL), dry over sodium sulfate and decant the liquid. Concentrate to a pale yellow oil (11.1; g) and distill using a Kügelrohr apparatus to give the title product as a colorless liquid (10.1; g, b.p.=140-150° C. at 2.4; mbar, 93%). MS (m/z): 202, 204; (M+1).

Preparation 27

Synthesis of (6-bromo-pyridin-2-yl)-dimethyl-amine

Heat a stirred mixture of 2,6-dibromopyridine (15; g, 63; mmol) and dimethylamine (40% aqueous solution, 21.4; mL, 190; mmol, 3; equiv) in ethanol (75; mL) for 3; days at 70° C. Evaporate the yellow solution to a reduced volume and dilute with ethyl acetate (100; mL). Wash with water (40; mL), brine (40; mL) and dry over sodium sulfate. Decant the liquid and evaporate to give pale yellow oil (13.8; g). Distill using a Kügelrohr apparatus to give the title product as a colorless liquid (12.4; g, b.p.=100-140° C. at 0.1 mbar). MS (m/z): 201, 203; (M+1).

Preparation 28

Synthesis of (6-bromo-pyridin-2-yl)-methyl-amine

Add a 2; M solution of methylamine in tetrahydrofuran (33.6; mL, 67.12; mmol) to 2,6-dibromopyridine (5.3; g, 22.37; mmol) and heat overnight at 110° C. in a sealed tube. Concentrate and purify by silica gel chromatography, gradient eluting from 0:100; to 20:80; ethyl acetate:iso-hexane to give the title compound (0.345; g, 8%) as a pale yellow oil which crystallizes on standing. MS (m/z): 185,187; (M+1).

Preparation 29

Synthesis of 2-bromo-6-difluoromethyl-pyridine

Add diethylaminosulfur trifluoride (31.5; mL, 0.238; mol) dropwise over 20; min to a stirring cooled solution of 6-bromo-pyridine-2-carbaldehyde (30.40; g, 0. 158; mol) in dichloromethane (600; mL) at 0° C. and warm to room temperature overnight. Divide the reaction mixture in two batches of equal volume for ease of working up. Slowly add, using extreme caution, a saturated aqueous solution of sodium bicarbonate over 30; min. Wash the aqueous layer once with dichloromethane. Dry the combined organic layers over sodium sulfate, filter, and concentrate. Purify resulting crude material by silica gel chromatography, gradient eluting from 1:99; to 10:90; using ethyl acetate:iso-hexane, to give the title compound (22.60; g, 68%) and a second fraction (9.4; g, 90% wt/wt purity, 26%) which are used with our further purification. $^1$H NMR (CDCl$_3$) δ 6.59; (t, 1H), 7.61 (m, 2H), 7.73(t, 1H).

The following compound is prepared essentially as described in Preparation 29.

| Preparation | Name | Data |
|---|---|---|
| 30 | 2-bromo-6-fluoromethyl-pyridine | GC-MS: 189, 191 (M+) |

Preparation 31

Synthesis of 2-(6-bromo-pyridin-2-yl)-propan-2-ol

Add a solution of methyl magnesium bromide (3.0; M, 9.7; mL, 29.09; mmol) in tetrahydrofuran dropwise over 20; min to a cooled solution of 1-(6-bromo-pyridin-2-yl)-ethanone (5; g, 24.25; mmol) in anhydrous tetrahydrofuran (48.5; mL) at 0° C. Upon completion of the reaction, add water (exothermic), dilute with ethyl acetate (50; mL) and separate the layers. Extract the aqueous layer once with ethyl acetate (50; mL). Dry the combined organic layers over sodium sulfate, filter and concentrate to give the title compound as a pale yellow liquid (5.69; g, 98%) that is used without further purification. $^1$H NMR (CDCl$_3$) δ 1.55; (s, 6H), 4.07; (s, 1H), 6.59; (t, 1H), 7.37; (t, 2H), 7.55; (t, 1H).

Preparation 32

Synthesis of 2-bromo-6-(1-fluoro-1-methyl-ethyl)-pyridine

Add (bis(2-methoxyethyl)amino)sulfur trifluoride (2.05; mL, 11.11; mmol) dropwise to a cooled solution of 2-(6-bromo-pyridin-2-yl)-propan-2-ol (2; g, 9.26 mmol) in dichloromethane (46.3; mL) at −78° C. Upon addition, warm to room temperature and stir overnight. Add a saturated aqueous solution of sodium bicarbonate and stir until gas evolution stops. Filter through a 50; mL hydrophobic IST Phase Separator Frit®, concentrate and purify by silica gel chromatography, gradient eluting from 3:97; to 5:95; and then to 10:90; using dichloromethane:iso-hexane to give the title compound as a colorless liquid (5.13; g, 71%). $^1$H NMR (CDCl$_3$) δ 1.66; (s, 3H), 1.73; (s, 3H), 7.37; (dd, 2H), 7.53; (m, 2H). $^{19}$F NMR (CDCl$_3$) δ-143.37; (s, 1F).

Preparation 33

Synthesis of 2-ethyl-6-tributylstannanyl-pyridine

Add under nitrogen a solution of tert-butyllithium in pentane (1.5; M, 80.3; mL, 120.5; mmol) dropwise over 1; hour to a cooled solution of 2-bromo-6-ethyl-pyridine (10.19; g, 54.77; mmol) in anhydrous diethyl ether (101.9; mL) at −78° C. at a rate so that the internal reaction temperature does not exceed −75° C. Stir 15; min and add tri-n-butyltin chloride (16.25; mL, 57.51; mmol) dropwise at a rate so that the internal reaction temperature does not exceed −70° C. Warm to room temperature, add water and separate the layers. Extract the aqueous phase once with diethyl ether. Dry the combined organic layers over sodium sulfate, filter and concentrate to give the title compound as a pale yellow liquid (24.05; g, 94%) that is subsequently used without further purification. $^1$H NMR (CDCl$_3$) δ 0.88; (t, 9H), 1.09; (m, 6H), 1.32; (m, 9H), 1.56; (m, 6H), 1.57; (m, 6H), 2.80; (q, 2H), 6.95; (m, 1H), 7.17; (d, 1H), 7.38; (t, 1H).

The following compounds are prepared essentially as described in Preparation 33 using 2-bromo-6-isopropyl-pyridine and 2-bromo-6-difluoromethyl-pyridine.

| Preparation | Name | Data |
|---|---|---|
| 34 | 2-isopropyl-6-tributylstannanyl-pyridine | MS (m/z): 408-417 cluster (M + 1) |
| 35 | 2-difluoromethyl-6-tributylstannanyl-pyridine | $^1$HNMR (CDCl$_3$) δ 0.88 (t, 9H), 1.12 (m, 6H), 1.33 (m, 6H), 1.56 (m, 6H), 6.63 (t, 1H), 7.47 (m, 2H), 7.61 (t, 1H) |

Preparation 36

Synthesis of dimethyl-(6-tributylstannanyl-pyridin-2-yl)-amine

Add dropwise a solution of (6-bromo-pyridin-2-yl)-dimethyl-amine (8; g, 39.8 mmol) in anhydrous tetrahydrofuran (10; mL) to a stirring cooled solution of n-butyl-lithium in hexanes (2.5; M, 19.1; mL, 47.7; mmol) in anhydrous tetrahydrofuran (160; mL) under nitrogen at −75° C. at a rate so that the internal reaction temperature does not exceed −70° C. After 1; h at −75° C., add dropwise tri-n-butyltin chloride (13; g, 39.8; mmol), stir for 30; min and warm to 0° C. Add water (200; mL) and then dilute with a saturated aqueous solution of sodium bicarbonate (50; mL) and diethyl ether (200; mL) and separate the layers. Extract the organic phase once with brine (200; mL), dry over sodium sulfate, filter and concentrate to give a liquid (25.4; g). Purify by silica gel chromatography eluting with iso-hexane:ethyl acetate:triethylamine 90:9:1, to give the title product as a colorless liquid (8.16; g, 50%). MS (m/z): 409-414; cluster (M+1).

EXAMPLE 1

Synthesis of (1R,2R)-2-methyl-cyclopropanecarboxylic acid [4-(6-ethyl-pyridin-2-yl)-3-(2-methyl-2H-indazol-5-yl)-isothiazol-5-yl]-amide

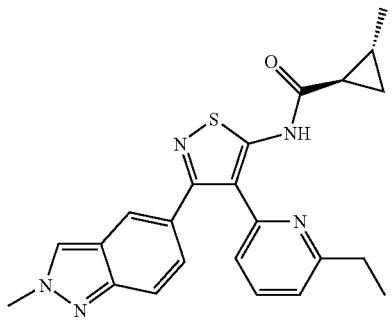

Dissolve (1R,2R)-2-methyl-cyclopropanecarboxylic acid [4-bromo-3-(2-methyl-2H-indazolyl-5-yl)-isothiazol-5-yl]-amide (288; g, 0.736; moles) in THF (2.9; L), add 2-ethyl-6-(tributylstannyl)pyridine (498.8; g, 1.10; moles), and sparge with a sub-surface nitrogen flow for 10; min. Add bis(triphenylphosphine) palladium (II) chloride (26.4; g, 36.8; mmol) and continue sparge for 5; min. Switch sparge to a nitrogen purge and heat the mixture to reflux. After 56.5; hours, cool the flask contents to ambient temperature and concentrate the solution under reduced pressure. Dissolve the resulting slurry in toluene (6; L) and add 1; N HCl (3; L). Filter the biphasic mixture across Whatman® GFF paper and transfer the filtrate to a bottom outlet flask. Separate the layers and back-extract the organics with 1; N HCl (3; L). Combine the aqueous layers and wash with toluene (6 L). To the aqueous layer, add 5N NaOH to pH 9. Separate the layers and wash the organics with brine (3; L). Dry the organics over MgSO$_4$, filter across Whatman® GFF paper and concentrate under reduced pressure to give a residue. Purify the residue using silica gel plug chromatography, eluting with acetonitrile:heptane:methylene chloride (20:30:50). Combine the appropriate fractions and concentrate under reduced pressure to afford the title compound as an amorphous foam. $^1$H NMR (CDCl$_3$, 400.0; MHz): δ 0.85 (m, 1H), 1.19; (d, 3H), 1.33; (m, 3H), 1.45; (t, 3H), 2.96; (q, 2H), 4.24; (s, 1H), 6.19, (d, 1H, J=8; Hz), 7.01; (d, 1H, J=8; Hz), 7.28; (dd, 1H, J=12; Hz), 7.33; (t, 1H, J=8; Hz), 7.66; (d, 1H, J=12; Hz), 7.89; (s, 1H), 7.94; (s, 1H), 13.0; (s, 1H).

Crystallization of (1R,2R)-2-methyl-cyclopropanecarboxylic acid [4-(6-ethyl-pyridin-2-yl)-3-(2-methyl-2H-indazol-5-yl)-isothiazol-5-yl]-amide.

Dissolve (1R,2R)-2-methyl-cyclopropanecarboxylic acid [4-(6-ethyl-pyridin-2-yl)-3-(2-methyl-2H-indazol-5-yl)-isothiazol-5-yl]-amide (113; mg, 270.6; μmol) in ethyl acetate (226; μL) with stirring and gentle warming. Add hexanes (339; μL) to the warm solution and allow the resulting mixture to stand while self-cooling to ambient temperature. Filter the resulting crystals and rinse with hexanes (0.5; mL). Vacuum dry the material at 35° C. to afford the title compound as a white crystalline solid. $^1$H NMR (CDCl$_3$, 400.0; MHz): δ 0.85; (m, 1H), 1.19; (d, 3H), 1.33; (m, 3H), 1.45; (t, 3H), 2.96; (q, 2H), 4.24; (s, 1H), 6.19, (d, 1H, J=8; Hz), 7.01; (d, 1H, J=8; Hz), 7.28; (dd, 1H, J=12 Hz), 7.33; (t, 1H, J=8; Hz), 7.66; (d, 1H, J=12; Hz), 7.89; (s, 1H), 7.94; (s, 1H), 13.0; (s, 1H).

Alternative method for the synthesis of (1R,2R)-2-methyl-cyclopropanecarboxylic acid [4-(6-ethyl-pyridin-2-yl)-3-(2-methyl-2H-indazol-5-yl)-isothiazol-5-yl]-amide.

Purge under nitrogen a solution of (1R,2R)-2-methyl-cyclopropanecarboxylic acid [4-bromo-3-(2-methyl-2H-indazol-5-yl)-isothiazol-5-yl]-amide (6.04; g, 13.28; mmol) and 2-ethyl-6-tributylstannanyl-pyridine (9.28; g, 19.91; mmol) in anhydrous 1,2-dimethoxyethane (52; mL) for 30; min and add bis(tri-t-butylphosphine)palladium (0) (0.35; g, 0.66; mmol) and heat at 100° C. under nitrogen for 4; days. Concentrate, dissolve residue in ethyl acetate and filter through a wet pad of Celite® using ethyl acetate. Concentrate and purify by silica gel chromatography, gradient eluting from 60:40; to 70:30; and then to 90:10; with ethyl acetate:isohexane and then neat ethyl acetate. Concentrate, dissolve in ethyl acetate (50; mL) and filter. Add a 2; M solution of hydrogen chloride in diethyl ether (6; mL) dropwise under nitrogen to the filtrate and stir for 30; min. Filter, wash the recovered solid with ethyl acetate (10; mL) and dry overnight. Dissolve in methanol (100; mL), divide in 3; fractions of equal volume and load each fraction onto an Isolute® SCX-2; column (20; g, Biotage AB) pre-washed with methanol. Wash with methanol (3; column volumes), elute with a 2; M solution of ammonia in methanol (1; column volume), combine and concentrate. Further purify by SFC [2-Ethylpyridine column (Princeton Chromatography Inc.), 60A, 7μ particle size, mobile phase 15% methanol (w/0.2% diethylmethylamine): 85% carbon dioxide, outlet pressure 100; bar] using methanol as an injection solvent [18; mL, scaled injection volume of 1.5 mL/injection (230; mg material per injection), injecting every 4; min to obtain a throughput of 3.5; g/h] to give the title compound (1.77; g, 32%). MS (m/z): 418; (M+1).

Trace amounts of heavy metals may be removed from the above purified title compound using the following protocol. Add CR20; Diaion® resin (28.86; g, Resindion-Mitsubichi Chemical) to a solution of the title compound (14.62; g, 34.56; mmol) in toluene (577.2; mL) with stirring and heat at 60° C. for 15; h. Cool to room temperature, filter and wash the recovered resin with toluene. Add fresh CR20; Diaion® resin (28.86; g) to the filtrate and stir at 60° C. for 7; hours. Cool to room temperature, filter, wash the recovered resin with toluene and concentrate to give a yellow solid (14.7; g). Dissolve the solid in methyl t-butyl ether (735; mL), wash twice with a saturated aqueous solution of potassium fluoride (43% wt/wt solution) for 10; min, dry over magnesium sulfate, filter and concentrate. Triturate the residue twice with hexanes (294; mL) with filtering and dry under vacuum to give the title compound as a white solid. MS (m/z): 418; (M+1).

EXAMPLE 2

Synthesis of (1R,2R)-2-methyl-cyclopropanecarboxylic acid [4-(6-ethyl-pyridin-2-yl)-3-(2-methyl-2H-indazol-5-yl)-isothiazol-5-yl]-amide hydrochloride

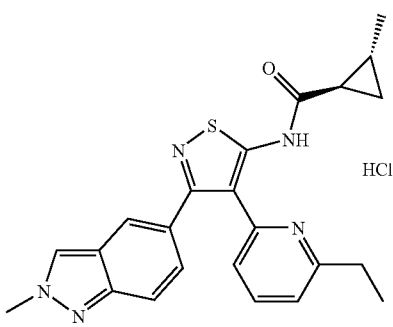

Add slowly via syringe a solution of 1; M hydrogen chloride in diethyl ether (25.92; mL, 25.92; mmol) to a stirring solution of (1R,2R)-2-methyl-cyclopropanecarboxylic acid

[4-(6-ethyl-pyridin-2-yl)-3-(2-methyl-2H-indazol-5-yl)-isothiazol-5-yl]-amide (11; g, 25.92; mmol) in ethyl acetate (135.30; mL) at room temperature to give a suspension. After 10; min, concentrate and further dry under high vacuum for 3; days to give the title compound as a white solid (11.92; g, 99%). MS (m/z): 418; (M-HCl+1). $^1$H NMR (DMSO-$d_6$) δ 0.86; (m, 1H), 1.10; (d, 3H), 1.17; (m, 1H), 1.27 (t, 3H), 1.39; (m, 1H), 1.91; (m, 1H), 3.02; (q, 2H), 7.16; (d, 1H), 7.81; (s, 1H), 7.51; (d, 3 H), 8.31; (s, 2; H), 12.20; (s, 1H).

EXAMPLE 3

Synthesis of (1R,2R)-2-methyl-cyclopropanecarboxylic acid [4-(6-isopropyl-pyridin-2-yl)-3-(2-methyl-2H-indazol-5-yl)-isothiazol-5-yl]-amide hydrochloride

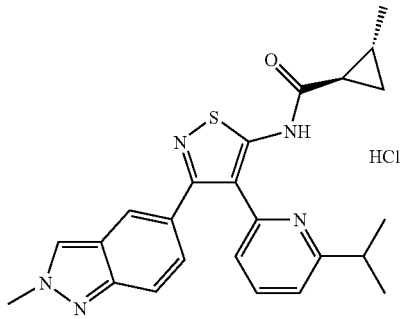

Purge under nitrogen a solution of (1R,2R)-2-methyl-cyclopropanecarboxylic acid [4-bromo-3-(2-methyl-2H-indazol-5-yl)-isothiazol-5-yl]-amide (6.31; g, 12.26; mmol) and 2-isopropyl-6-tributylstannanyl-pyridine (15.08; g, 18.38; mmol) in anhydrous 1,2-dimethoxyethane (50; mL) for 60; min and add bis(tri-t-butylphosphine)palladium (0) (0.32; g, 0.61; mmol). Stir at 100° C. under nitrogen for 3; days, concentrate to a reduced volume and dilute with ethyl acetate (50; mL). Filter through a pad of Celite®, concentrate to a dark brown oil and purify by silica gel chromatography, gradient eluting from 60:40 to 90:10; using ethyl acetate:iso-hexane to give a light brown oil (7.3; g). Dissolve in ethyl acetate (40; mL) and add a 2; M solution hydrogen chloride in diethyl ether (4.5; mL, 9; mmol) to give a precipitate. Filter to give a cream colored solid (4.14; g). Dissolve in methanol (15; mL), divide into three portions and load each portion onto an Isolute SCX-2® column (20; g, Biotage AB). Wash with methanol (120; mL per column) and elute from the column using a 2M solution of ammonia in methanol (100; mL per column). Concentrate to a yellow foam and purify by silica gel chromatography, gradient eluting from 70:30; to 80:20; using ethyl acetate:iso-hexane to give the free base of the title product as a yellow oil. Dissolve in ethyl acetate (40; mL), and add a 2; M solution of hydrogen chloride in diethyl ether (4.5; mL, 9; mmol) to give an immediate precipitate. Allow to stand for 1; hour then filter to give the title compound as a white powdery solid (3.85; g, 65%). MS (m/z): 432; (M-HCl+1).

The following compound is prepared essentially as described in Example 3.

| Example | Name | Data |
|---------|------|------|
| 4 | (1R,2R)-2-methyl-cyclopropanecarboxylic acid [4-(6-difluoromethyl-pyridin-2-yl)-3-(2-methyl-2H-indazol-5-yl)-isothiazol-5-yl]-amide hydrochloride | MS (m/z): 440 (M − HCl + 1) |

EXAMPLE 5

Synthesis of (1R,2R)-2-methyl-cyclopropanecarboxylic acid [3-(2-methyl-2H-indazol-5-yl)-4-pyridin-2-yl-isothiazol-5-yl]-amide hydrochloride

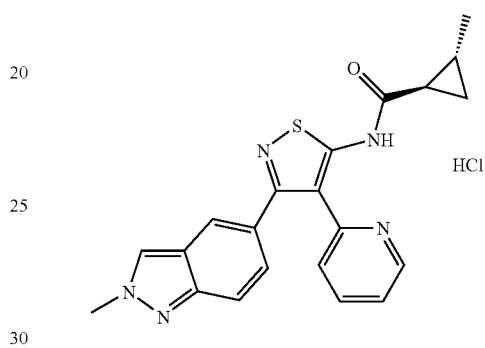

Degas, by bubbling nitrogen for 10; min through a mixture of tributyl-2-pyridinyltin (244; μL, 0.70; mmol) and (1R,2R)-2-methyl-cyclopropanecarboxylic acid [4-bromo-3-(2-methyl-2H-indazol-5-yl)-isothiazol-5-yl]-amide (0.25; g, 0.64; mmol) in anhydrous 1,2-dimethoxyethane (5.00; mL), add bis(tri-t-butylphosphine)palladium (0) (0.02; g, 31.95; μmol) and stir at 100° C. under nitrogen overnight. Cool the reaction mixture to room temperature, add a 10% aqueous solution of potassium fluoride (3; mL), stir 10; min and extract with ethyl acetate. Wash the organic layers with brine, dry over magnesium sulfate, filter and concentrate to dryness. Purify the residue by silica gel chromatography, gradient eluting from 0:100; to 100:0; using ethyl acetate:iso-hexane, and then further purify by reverse phase HPLC (water w/ammonium bicarbonate (pH=9)/acetonitrile) to give the free base as a colorless oil. Dissolve in ethyl acetate (1; mL), add a 1; M solution of hydrogen chloride in diethyl ether (250; μL) and concentrate under vacuum to give the title compound as a white solid (111; mg). MS (m/z): 390; (M-HCl+1).

The following compounds are prepared essentially as described in Example 5 using (6-bromo-pyridin-2-yl)-dimethyl-amine and either (1R,2R)-2-methyl-cyclopropanecarboxylic acid [4-bromo-3-(2-ethyl-2H-indazol-5-yl)-isothiazol-5-yl]-amide or (1R,2R)-2-methyl-cyclopropanecarboxylic acid [4-bromo-3-(2-methyl-2H-indazol-5-yl)-isothiazol-5-yl]-amide. Example 7; is prepared as the free base by omitting treatment with hydrogen chloride.

| Example | Name | Data |
|---------|------|------|
| 6 | (1R,2R)-2-methyl-cyclopropanecarboxylic acid [4-(6-dimethylamino-pyridin-2-yl)-3-(2-ethyl-2H-indazol-5-yl)-isothiazol-5-yl]-amide hydrochloride | MS (m/z): 447 (M − HCl + 1) |

| Example | Name | Data |
|---|---|---|
| 7 | (1R,2R)-2-methyl-cyclopropanecarboxylic acid [4-(6-dimethylamino-pyridin-2-yl)-3-(2-methyl-2H-indazol-5-yl)-isothiazol-5-yl]-amide | MS (m/z): 440 (M + 1) |

EXAMPLE 8

Synthesis of (1R,2R)-2-methyl-cyclopropanecarboxylic acid [3-(1H-indazol-5-yl)-4-(6-isopropyl-pyridin-2-yl)-isothiazol-5-yl]-amide hydrochloride

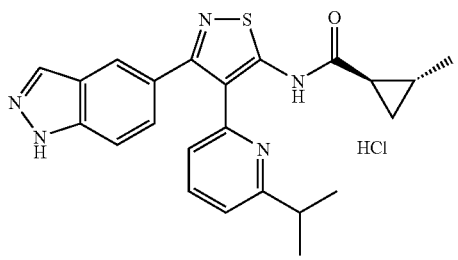

Add bis(tri-t-butylphosphine)palladium (0) (7.4; mg, 0.01; mmol) to a stirring solution of 5-{4-bromo-5-[((1R,2R)-2-methyl-cyclopropanecarbonyl)-amino]-isothiazol-3-yl}-indazole-1-carboxylic acid tert-butyl ester (0.33; g, 0.48; mmol) and 2-isopropyl-6-tributylstannanyl-pyridine (0.308; g, 0.64; mmol) in anhydrous 1,2-dimethoxyethane (2.4 mL) under nitrogen and heat at 80° C. for 18; hours. Purify the reaction solution directly by silica gel chromatography, gradient eluting from 20:80; to 60:40; using ethyl acetate:hexanes to give the freebase of the title compound (78; mg, 34%) and 5-{4-(6-isopropyl-pyridin-2-yl)-5-[((1R,2R)-2-methyl-cyclopropane carbonyl)-amino]-isothiazol-3-yl}-indazole-1-carboxylic acid tert-butyl ester (85; mg, 29%). MS (m/z): 518; (M+1).

Dissolve the isolated 5-{4-(6-isopropyl-pyridin-2-yl)-5-[((1R,2R)-2-methyl-cyclopropane carbonyl)-amino]-isothiazol-3-yl}-indazole-1-carboxylic acid tert-butyl ester (83; mg, 0.16; mmol) in dichloromethane (2; mL), add trifluoroacetic acid (2; mL) and stir for 2; hours. Concentrate and purify by silica gel chromatography, gradient eluting from 20:80; to 30:70; using ethyl acetate:(50:50; dichloromethane/hexanes) to give the free base of the title compound (47; mg). MS (m/z): 418; (M+1).

Combine the two batches of the free base of the title compound (125; mg, 0.3 mmol), slurry in diethyl ether (4; mL) and add methanol to dissolve. Add a 1; N solution of hydrogen chloride in diethyl ether (0.3; mL, 0.3; mmol) and concentrate. Dry under vacuum to give the title compound (92; mg, 42% over two steps). MS (m/z): 418; (M-HCl+1).

EXAMPLE 9

Synthesis of (1R,2R)-2-methyl-cyclopropanecarboxylic acid [4-(6-cyclobutyl-pyridin-2-yl)-3-(2-methyl-2H-indazol-5-yl)-isothiazol-5-yl]-amide hydrochloride

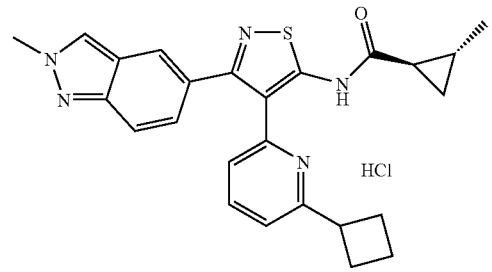

Add to a microwave vessel 2-bromo-6-cyclobutyl-pyridine (0.18; g, 0.84; mmol), hexamethylditin (0.18; mL, 0.84; mmol), lithium chloride (97.5; mg, 2.30; mmol) and anhydrous 1,4-dioxane (2.5; mL) and degas by bubbling nitrogen. Add tetrakis(triphenylphosphine) palladium (44.3; mg, 38.33; μmol) and heat in a microwave with stirring at 110° C. for 5; min. to give a solution of 2-cyclobutyl-6-tributylstannanyl-pyridine.

Sequentially add to the above solution a degassed solution of (1R,2R)-2-methyl-cyclopropanecarboxylic acid [4-bromo-3-(2-methyl-2H-indazol-5-yl)-isothiazol-5-yl]-amide (0.30; g, 0.77; mmol) in anhydrous 1,2-dimethoxyethane (2.5; mL) and bis(tri-t-butylphosphine)palladium (0) (0.05; g, 0.98; mmol). Heat in a microwave at 100° C. with stirring for 2; hours. Purify the reaction mixture directly by silica gel chromatography, gradient eluting from 60:40; to 100:0; using ethyl acetate:iso-hexane and then further purify by a second silica gel chromatography, gradient eluting from 100:0; to 97:3; using dichloromethane:methanol to give the free base of the title compound. Dissolve in a minimum amount of dichloromethane, add a 2; M solution of hydrogen chloride (0.11; mL, 0.22; mmol) in diethyl ether and concentrate to dryness to give the title compound (88.80 mg, 24%) as a white solid. MS (m/z): 444; (M-HCl+1).

The following compounds are prepared essentially as described in Example 9 from (1R,2R)-2-methyl-cyclopropanecarboxylic acid [4-bromo-3-(2-methyl-2H-indazol-5-yl)-isothiazol-5-yl]-amide and the corresponding 2-bromo-6-substituted-pyridine

| Example | Name | Data |
|---|---|---|
| 10 | (1R,2R)-2-methyl-cyclopropanecarboxylic acid [4-(6-cyclopropyl-pyridin-2-yl)-3-(2-methyl-2H-indazol-5-yl)-isothiazol-5-yl]-amide hydrochloride | MS (m/z): 430 (M − HCl + 1) |
| 11 | (1R,2R)-2-methyl-cyclopropanecarboxylic acid [4-[6-(1-fluoro-1-methyl-ethyl)-pyridin-2-yl]-3-(2-methyl-2H-indazol-5-yl)-isothiazol-5-yl]-amide hydrochloride | MS (m/z): 450 (M − HCl + 1) |
| 12 | (1R,2R)-2-methyl-cyclopropanecarboxylic acid [4-(6-methyl-pyridin-2-yl)-3-(2-methyl-2H-indazol-5-yl)-isothiazol-5-yl]-amide hydrochloride | MS (m/z): 404 (M − HCl + 1) |

| Example | Name | Data |
|---|---|---|
| 13 | (1R,2R)-2-methyl-cyclopropanecarboxylic acid [4-(6-methylamino-pyridin-2-yl)-3-(2-methyl-2H-indazol-5-yl)-isothiazol-5-yl]-amide hydrochloride | MS (m/z): 419 (M – HCl + 1) |

The following compounds are prepared essentially as described in Example 9 from (1R,2R)-2-methyl-cyclopropanecarboxylic acid [4-bromo-3-(2-methyl-2H-indazol-5-yl)-isothiazol-5-yl]-amide and the corresponding 2-bromo-6-substituted-pyridine and isolated as their free base.

| Example | Name | Data |
|---|---|---|
| 14 | (1R,2R)-2-methyl-cyclopropanecarboxylic acid [3-(2-methyl-2H-indazol-5-yl)-4-(6-propyl-pyridin-2-yl)-isothiazol-5-yl]-amide | MS (m/z): 432 (M + 1) |
| 15 | (1R,2R)-2-methyl-cyclopropanecarboxylic acid [4-(6-cyclopentyl-pyridin-2-yl)-3-(2-methyl-2H-indazol-5-yl)-isothiazol-5-yl]-amide | MS (m/z): 458 (M + 1) |
| 16 | (1R,2R)-2-methyl-cyclopropanecarboxylic acid [4-(6-fluoromethyl-pyridin-2-yl)-3-(2-methyl-2H-indazol-5-yl)-isothiazol-5-yl]-amide | MS (m/z): 422 (M + 1) |
| 17 | (1R,2R)-2-methyl-cyclopropanecarboxylic acid [4-(6-methoxymethyl-pyridin-2-yl)-3-(2-methyl-2H-indazol-5-yl)-isothiazol-5-yl]-amide | MS (m/z): 434 (M + 1) |

EXAMPLE 18

Synthesis of cyclopropanecarboxylic acid [4-(6-dimethylamino-pyridin-2-yl)-3-(2-methyl-2H-indazol-5-yl)-isothiazol-5-yl]-amide hydrochloride

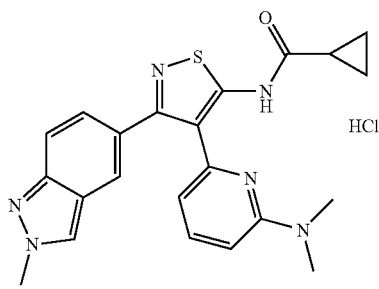

Degas, by bubbling nitrogen through a mixture of dimethyl-(6-tributylstannanyl-pyridin-2-yl)-amine (0.34; g, 0.84; mmol) and cyclopropanecarboxylic acid [4-bromo-3-(2-methyl-2H-indazol-5-yl)-isothiazol-5-yl]-amide (0.24; g, 0.64; mmol) in 1,2-dimethoxyethane (3; mL) for 10; min, add bis(tri-t-butylphosphine)palladium(0) (0.02 g, 32.21; μmol) and stir at 100° C. under nitrogen overnight. Cool to room temperature, add a 10% aqueous solution of potassium fluoride (3; mL), stir 40; min and extract with ethyl acetate. Wash the organic layer with brine, dry over magnesium sulfate, filter and concentrate. Purify by ion exchange chromatography on an Isolute SCX-2® column (10 g, Biotage AB) as essentially described in Example 3, and then further purify by silica gel chromatography, gradient eluting from 0:100; to 80:20; using ethyl acetate:iso-hexane and purify further still by reverse phase HPLC (water w/ammonium bicarbonate (pH=9)/acetonitrile) to give the free base of the title compound. Dissolve in methanol, add a 1; M solution of hydrogen chloride in diethyl ether (240; μL, 0.24; mmol) and concentrate under vacuum to give the title compound as a pale yellow solid (0.11; g, 0.24; mmol). MS (m/z): 419; (M+1).

EXAMPLE 19

Synthesis of cyclopropanecarboxylic acid [4-(6-ethyl-pyridin-2-yl)-3-(2-methyl-2H-indazol-5-yl)-isothiazol-5-yl]-amide hydrochloride

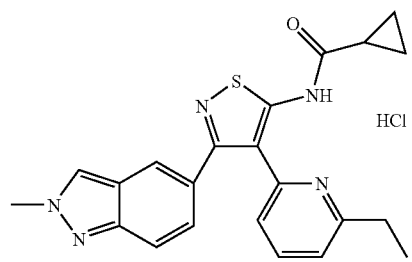

Degas by bubbling nitrogen for 10; min through a mixture of cyclopropanecarboxylic acid [4-bromo-3-(2-methyl-2H-indazol-5-yl)-isothiazol-5-yl]-amide (0.3; g, 0.79; mmol) and 2-ethyl-6-tributylstannanyl-pyridine (2.0; g, 5.05; mmol) in anhydrous 1,2-dimethoxyethane (4; mL). Add bis(tri-t-butylphosphine)palladium(0) (41 mg, 0.79; mmol), heat to 80° C. and stir for 20; h. Let cool to ambient temperature and purify directly by silica gel chromatography, gradient eluting from 50:50; to 100:0; using hexanes:ethyl acetate and then further purify by reversed phase HPLC (Kromasil® KR100-10C18-250P2, 50.8; mm×25; cm, flow rate 60; mL/min), gradient eluting from 15:85; to 80:20; using water (w/0.1% trifluoroacetic acid)/acetonitrile (w/0.1% trifluoroacetic acid) over 60; min. Combine fractions, make basic with a saturated aqueous solution of sodium bicarbonate, extract with dichloromethane twice, dry over anhydrous sodium sulfate, filter, and concentrate to give a solid (0.132; g, 0.33; mmol). Dissolve in dichloromethane (1.6; mL), cool at 0° C. and add a 1; M solution of hydrogen chloride in diethyl ether (0.327; mL, 0.33; mmol) with stirring. After 10; min, concentrate under vacuum, triturate the residue twice with diethyl ether and dry under vacuum to give the title compound as a solid (0.111; g, 0.25; mmol). MS (m/z): 404; (M-HCl+1).

The following compound is prepared essentially as described in Example 19; using 2-isopropyl-6-tributylstannanyl-pyridine.

| Example | Name | Data |
|---|---|---|
| 20 | cyclopropanecarboxylic acid [4-(6-isopropyl-pyridin-2-yl)-3-(2-methyl-2H-indazol-5-yl)-isothiazol-5-yl]-amide hydrochloride | MS (m/z): 418 (M – HCl + 1). |

EXAMPLE 21

Synthesis of (1R,2R)-2-methyl-cyclopropanecarboxylic acid [4-(6-methoxy-pyridin-2-yl)-3-(2-methyl-2H-indazol-5-yl)-isothiazol-5-yl]-amide

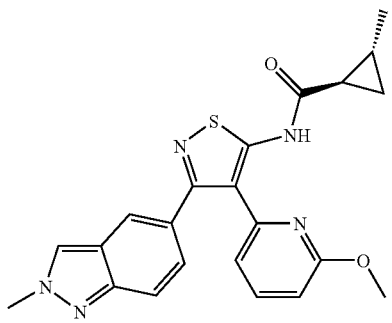

Add a 0.5M solution of 6-methoxy-2-pyridylzinc bromide in tetrahydrofuran (6.13 mL, 3.07; mmol) to a solution of (1R,2R)-2-methyl-cyclopropanecarboxylic acid [4-bromo-3-(2-methyl-2H-indazol-5-yl)-isothiazol-5-yl]-amide (0.24; g, 0.61; mmol) in anhydrous 1,2-dimethoxyethane (3.1; mL) and degas by bubbling with nitrogen for 20 min. Add bis(tri-t-butylphosphine)palladium (0) (0.01; g, 12.27; μmol), stir at room temperature under nitrogen overnight and then heat at 55° C. for 48; h. Dilute with brine and extract with ethyl acetate. Dry the ethyl acetate layers over magnesium sulfate, filter and concentrate. Purify by silica gel chromatography, gradient eluting from 0:100; to 30:70; eluting using ethyl acetate:chloroform and then further purify by reverse phase HPLC (water w/ammonium bicarbonate (pH=9)/acetonitrile) to give the title compound (29.6; mg). $^1$H NMR (CD$_3$OD) δ 0.85; (m, 1H), 1.18; (d, 3H), 1.35; (m, 1H), 1.44 (m, 1H), 1.62; (m, 1H), 4.11; (s, 3H), 4.24; (s, 3H) 6.57; (d, 1H), 6.62; (d, 1H), 7.27; (m, 1H), 7.34; (t, 1H), 7.65; (d, 1H), 7.91; (d, 2H), 12.17; (bs, 1H).

EXAMPLE 22

Crystallization of (1R,2R)-2-methyl-cyclopropanecarboxylic acid [4-(6-ethyl-pyridin-2-yl)-3-(2-methyl-2H-indazol-5-yl)-isothiazol-5-yl]-amide Dissolve (1R,2R)-2-methyl-cyclopropanecarboxylic acid [4-(6-ethyl-pyridin-2-yl)-3-(2-methyl-2H-indazol-5-yl)-isothiazol-5-yl]-amide (185; g, 0.44; mol) in ethyl acetate (555; mL) with stirring. Add seed crystals of Example 1; (200; mg) followed by hexanes (800; mL). Stir the resulting mixture at ambient temperature for 30; minutes. Filter the resulting crystals and rinse with hexanes (50; mL). Dry the solids in a vacuum oven at 35° C. to afford the title compound as a white crystalline solid. MS (m/z ): 418 (M+1); DSC (onset) mp=159.4° C.

EXAMPLE 23

Synthesis of (1R,2R)-2-methyl-cyclopropanecarboxylic acid [4-(6-isopropyl-pyridin-2-yl)-3-(2-methyl-2H-indazol-5-yl)-isothiazol-5-yl]-amide Equip a 3; L 3-neck round bottom flask with overhead agitation, thermocouple, condenser, heating mantle, and nitrogen purge. Charge the flask with (1R,2R)-2-methyl-cyclopropanecarboxylic acid [4-bromo-3-(2-methyl-2H-indazol-5-yl)-isothiazol-5-yl]-amide (96; g, 0.25; moles) and THF (1; L). Add 2-isopropyl-6-(tributylstannyl)pyridine (182; g, 0.44; moles) and agitate. Sparge with nitrogen at sub-surface for 20; minutes. Add bis(triphenylphosphine)palladium (II) chloride (8.62; g, 0.012; moles) and continue nitrogen sparge for 5; minutes. Switch sparge to a nitrogen purge and heat the vessel contents to reflux.

Stir the reaction mixture for 3; days at reflux condition (ca. 37% starting material remaining by LCMS). Cool the reaction mixture to 35° C., degas for 15; min, and add additional palladium catalyst (1; mol %). Stir the reaction for 2; days at reflux condition (22% starting material remaining by LC/MS). Cool the reaction mixture to 35° C., degas for 15; min, and add additional palladium catalyst (4; mol %). Stir the reaction for 2; days at reflux (13% starting material remaining by LC/MS). Cool the reaction mixture to 35° C., degas for 15; min, and add additional palladium catalyst (5; mol %). Stir the reaction for 4.5; hours at reflux (11% starting material remained by LC/MS). Cool the reaction mixture to 35° C., degas for 15; min, and add additional palladium catalyst (5; mol %). Once again stir for 15; hours at reflux (ca. 6% starting material remaining by LC/MS). Concentrate the solution in vacuo to remove solvent. Treat the resulting slurry with toluene (2; L) and 1; N HCl (1; L). Filter the biphasic mixture through Celite®. Separate the layers and back-extract the organic layer with 1; N HCl (1; L×3). Combine the aqueous layers and extract with toluene (1; L). Subsequently, treat the aqueous layer with toluene (2; L) and 5; N NaOH to pH=11. Separate the layers and extract the aqueous layer with toluene (1; L×2). Wash the combined organic layers with brine (700; mL), dry over sodium sulfate, and filter. Evaporate the filtrate in vacuo to afford the crude product as a yellow oil (78; g, 63% purity). Purify the crude material by flash chromatography (silica gel, ethyl acetate/hexanes) to provide the title product. Further purify by crystallization from ethyl acetate and hexanes. Combine lots and treat with toluene (500 mL) and 1; N HCl (250; mL). Separate the layers and back-extract with 1; N HCl (3×250 mL). Combine the aqueous layers and extract with toluene (300; mL). Treat the aqueous layer with toluene (500; mL) and 5; N NaOH to pH=11. Separate the layers and extract the aqueous layer with toluene (2×500; mL). Wash the combined organic layers with brine (200; mL), dry over sodium sulfate, and filter. Concentrate the filtrate in vacuo. Crystallize the resulting residue from ethyl acetate and hexanes to provide 40; g of the title compound as a white solid. mp=142°-144° C. MS (ES), m/z 432; (M+1).

We claim:
1. A compound of the formula, or a pharmaceutically acceptable salt thereof,

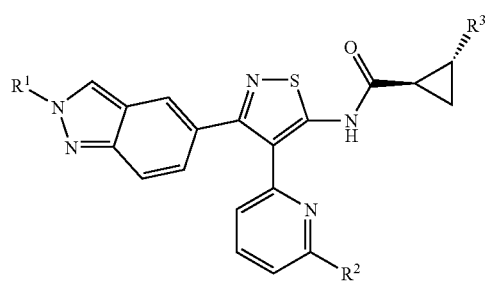

wherein
$R^1$ is H or $C_1$-$C_3$ alkyl;
$R^2$ is H, $C_1$-$C_3$ alkyl, $C_3$-$C_5$ cycloalkyl, $C_1$-$C_3$ fluoroalkyl, $NR^4R^5$, $C_1$-$C_3$ alkoxy or $C_1$-$C_3$ alkoxymethyl;
$R^3$ is H or methyl; and
$R^4$ and $R^5$ are independently H or $C_1$-$C_3$ alkyl.

2. The compound of claim 1, or a pharmaceutically acceptable salt thereof, wherein
$R^1$ is $C_1$-$C_3$ alkyl;
$R^2$ is $C_1$-$C_3$ alkyl, $C_3$-$C_5$ cycloalkyl or $C_1$-$C_3$ fluoroalkyl; and
$R^3$ is methyl.

3. The compound of claim 1, or a pharmaceutically acceptable salt thereof, wherein
$R^1$ is $C_1$-$C_3$ alkyl;
$R^2$ is $C_1$-$C_3$ alkyl; and
$R^3$ is methyl.

4. The compound of claim 1, or a pharmaceutically acceptable salt thereof, wherein
$R^1$ is $C_1$-$C_3$ alkyl.

5. The compound of claim 1, or a pharmaceutically acceptable salt thereof, wherein
$R^2$ is $C_1$-$C_3$ alkyl.

6. The compound of claim 1, 4 or 5, or a pharmaceutically acceptable salt thereof, wherein $R^3$ is methyl.

7. The compound of claim 1, or a pharmaceutically acceptable salt thereof, wherein
$R^1$ is H, methyl or ethyl;
$R^2$ is H, methyl, ethyl, propyl, isopropyl, cyclopropyl, cyclobutyl, cyclopentyl, fluoromethyl, difluoromethyl, 1-fluoro-1-methyl-ethyl, methylamino, dimethylamino, methoxy or methoxymethyl; and
$R^3$ is H or methyl.

8. The compound as claimed in claim 1 which is (1R,2R)-2-methyl-cyclopropanecarboxylic acid [4-(6-ethyl-pyridin-2-yl)-3-(2-methyl-2H-indazol-5-yl)-isothiazol-5-yl]-amide or a pharmaceutically acceptable salt thereof.

9. The compound as claimed in claim 1 which is (1R,2R)-2-methyl-cyclopropanecarboxylic acid [4-(6-isopropyl-pyridin-2-yl)-3-(2-methyl-2H-indazol-5-yl)-isothiazol-5-yl]-amide or a pharmaceutically acceptable salt thereof.

10. The compound as claimed in claim 9 which is (1R,2R)-2-methyl-cyclopropanecarboxylic acid [4-(6-isopropyl-pyridin-2-yl)-3-(2-methyl-2H-indazol-5-yl)-isothiazol-5-yl]-amide.

11. A pharmaceutical composition comprising a compound as claimed in claim 1, or a pharmaceutically acceptable salt thereof, and a pharmaceutically acceptable carrier, diluent or excipient.

12. A method of treating anxiety, comprising administering to a patient in need thereof an effective amount of a compound as claimed in claim 1, or a pharmaceutically acceptable salt thereof.

* * * * *